US009671388B2

(12) United States Patent
Lee et al.

(10) Patent No.: US 9,671,388 B2
(45) Date of Patent: Jun. 6, 2017

(54) APPARATUS AND METHOD FOR BLOOD ANALYSIS

(71) Applicants: ELECTRONICS AND TELECOMMUNICATIONS RESEARCH INSTITUTE, Daejeon (KR); PUSAN NATIONAL UNIVERSITY INDUSTRY-UNIVERSITY COOPERATION, Busan (KR)

(72) Inventors: Dae-Sik Lee, Daejeon (KR); Jeung Sang Go, Busan (KR); Mun Youn Jung, Daejeon (KR)

(73) Assignees: ELECTRONICS AND TELECOMMUNICATIONS RESEARCH INSTITUTE, Daejeon (KR); PUSAN NATIONAL UNIVERSITY INDUSTRY-UNIVERSITY COOPERATION, Busan (KR)

( * ) Notice: Subject to any disclaimer, the term of this patent is extended or adjusted under 35 U.S.C. 154(b) by 19 days.

(21) Appl. No.: 14/731,295

(22) Filed: Jun. 4, 2015

(65) Prior Publication Data
US 2016/0139106 A1   May 19, 2016

(30) Foreign Application Priority Data
Nov. 14, 2014   (KR) ........................ 10-2014-0158690

(51) Int. Cl.
*G01N 33/49*  (2006.01)
*G01N 1/28*   (2006.01)
(Continued)

(52) U.S. Cl.
CPC ........... *G01N 33/49* (2013.01); *G01N 1/2813* (2013.01); *G01N 11/04* (2013.01); *G01N 21/84* (2013.01);
(Continued)

(58) Field of Classification Search
CPC ..................................................... G01N 33/49
See application file for complete search history.

(56) References Cited

U.S. PATENT DOCUMENTS 5,168,021 A * 12/1992 Arai ........................ G03F 7/168
                                                       250/442.11
5,805,866 A *  9/1998 Magome ............. G03F 7/70858
                                                        355/53
(Continued)

FOREIGN PATENT DOCUMENTS

DE   10 2005 048 236 A1   4/2007
KR   10-2008-0047409 A    5/2008
(Continued)

OTHER PUBLICATIONS

Myounggon Kim et al., "Improvement of the accuracy of continuous hematocrit measurement under various blood flow conditions", Applied Physics Letters, Apr. 17, 2014, pp. 153508-1-153508-5, vol. 14, AIP Publishing LLC.
(Continued)

*Primary Examiner* — Tarifur Chowdhury
*Assistant Examiner* — Omar Nixon

(57) ABSTRACT

Provided is an apparatus for blood analysis. The apparatus for blood analysis includes a spin coater to which blood is supplied, a light source part emitting light onto the spin coater, a measurement part detecting light reflected from the blood on the spin coater, and outputting a detected signal, and an analysis part analyzing information on the blood from the detected signal from the measurement part.

18 Claims, 6 Drawing Sheets

(51) Int. Cl.
*G01N 21/84* (2006.01)
*G01N 11/04* (2006.01)
*G01N 11/00* (2006.01)

(52) U.S. Cl.
CPC ......... *G01N 21/8422* (2013.01); *G01N 11/00* (2013.01)

(56) References Cited

U.S. PATENT DOCUMENTS

| | | | |
|---|---|---|---|
| 2004/0266169 A1* | 12/2004 | Sakata | H01L 21/76807 438/622 |
| 2008/0280365 A1 | 11/2008 | Grumann et al. | |
| 2009/0027640 A1* | 1/2009 | Shibazaki | G03F 7/70775 355/53 |
| 2009/0139651 A1* | 6/2009 | Fujii | G11B 7/266 156/280 |
| 2010/0157295 A1 | 6/2010 | Ko et al. | |
| 2010/0157300 A1 | 6/2010 | Lee et al. | |
| 2013/0110405 A1 | 5/2013 | Yang et al. | |

FOREIGN PATENT DOCUMENTS

| | | |
|---|---|---|
| KR | 10-2011-0039823 A | 4/2011 |
| KR | 10-2013-0046143 A | 5/2013 |

OTHER PUBLICATIONS

M. Jedrzejewska-Szczerska et al., "Spectroscopic wireless sensor of hematocrit level", Sensors and Actuators A: Physical, Apr. 19, 2013, pp. 8-12, vol. 202, Elsevier.

* cited by examiner

FIG. 5

| Solution Color | Orange | Dark Orange | Red | Dark Red |
|---|---|---|---|---|
| Hematocrit Number (Volume of blood cell in plasma) | Low Concentration | → | | High Concentration |

…

APPARATUS AND METHOD FOR BLOOD ANALYSIS

CROSS-REFERENCE TO RELATED APPLICATIONS

This U.S. non-provisional patent application claims priority under 35 U.S.C. §119 of Korean Patent Application No. 10-2014-0158690, filed on Nov. 14, 2014, the entire contents of which are hereby incorporated by reference.

BACKGROUND OF THE INVENTION

The present invention relates to an apparatus and a method for blood analysis, and more specifically, to an apparatus and a method for blood analysis using a spin coater.

Blood has viscosity. The principal components that determine the viscosity of blood are blood cells and plasma. There are various types of viscometers. In capillary viscometers, the time taken for a predetermined volume of test fluid to flow through a narrow tube is measured, the flow rate (the amount of flow) of a standard fluid is measured by allowing the fluid to flow, and the coefficient of viscosity is determined by applying Poiseuille's law. In addition, there are viscometers such as falling sphere viscometers in which the falling speed of a small ball in a stationary fluid is measured and Stoke's law is applied, bubble viscometers in which the rising speed of an air bubble is measured, rotational viscometers in which a fluid is filled between concentric cylinders and viscous resistance is measured by rotating an inner cylinder, vibrational viscometers in which the damping of a torsional vibration of a vibrating body in a fluid is measured, and Engler viscometers in which an Engler degree is measured. These viscometers are relatively expensive, need a long analysis time, and require a large amount of a sample for analysis.

The hematocrit (HCT) is the volume percentage of red blood cells in blood. It is normally about 45-52% for men and about 37-47% for women. A blood sample is injected into a glass capillary tube and is rotated at high speed, and then the red blood cell components in the blood are separated from plasma and packed into a layer. The length covered by the red cells in the blood sample in the capillary tube is the hematocrit. The hematocrit of blood is an indicator for blood properties such as the degree of blood circulation and anemia. Typically, a hematocrit measurement through centrifugation takes a long time and requires a long analysis time.

The mean volume percentage and the number of individual red blood cells can be measured by using an electrical signal. In the case of a Coulter counter, the volume percentage of red blood cells can be measured from measured information. However, the method using a Coulter counter is expensive, and Coulter counters are bulky and difficult to carry.

SUMMARY OF THE INVENTION

The present invention provides an apparatus and a method for blood analysis using a spin coater.

Embodiments of the present invention provide an apparatus for blood analysis. The apparatus for blood analysis includes a spin coater to which blood is supplied, a light source part emitting light to the spin coater, a measurement part detecting light reflected from the blood on the spin coater and outputting a detected signal, and an analysis part analyzing information on the blood from the detected signal of the measurement part.

In some embodiments, a spin substrate of the spin coater may have a concave portion inclined toward a central axis of the substrate.

In other embodiments, a spin substrate of the spin coater may have at least one ring-shaped groove spaced apart from each other.

In still other embodiments, the measurement part may obtain images of the blood spread on the spin coater by means of a rotation of the spin coater and the groove and may analyze a viscosity of the blood located in the groove from the images.

In even other embodiments, the spin substrate may be formed of at least one of metal, ceramic, polymer, and glass.

In yet other embodiments, the polymer may include at least one of polymethyl methacrylate (PMMA), polyimide (PI), polycarbonate (PC) and cyclo olefin copolymer (COC).

In further embodiments, the analysis part may determine a color of the blood from the detected signal, and may analyze a volume of blood cells in the blood corresponding to the color.

In still further embodiments, the measurement part may momentarily supply pressure to a blood cell in the blood to continuously capture deformation of the blood cell.

In even further embodiments, the measurement part may comprise a light receiving portion receiving light reflected from the spin coater, and an image processing portion transforming the light received by the light receiving portion into an image signal.

In yet further embodiments, the light receiving portion may comprise one of a photodiode, a CIS and a CCD.

In much further embodiments, the measurement part may further comprise a drive portion which moves the light receiving portion toward the spin coater.

In still much further embodiments, the information on the blood may comprise a viscosity of the blood, a color of the blood, and an elastic modulus of the blood.

Other embodiments of the present invention provide a method for blood analysis. A method for blood analysis comprises: dropping a solution onto a spin coater; rotating the spin coater; and measuring a varying state of the solution on the rotating spin coater.

In some embodiments, the measuring may comprise measuring a viscosity of the solution by measuring a spread area of the solution in the spin coater.

In other embodiments, the rotating of the spin coater may comprise gradually increasing a rotational speed of the spin coater, and the measuring may comprise measuring a viscosity of the solution by capturing a state of the solution.

In still other embodiments, the measuring may comprise measuring a hematocrit by measuring a reflected color after emitting light onto a portion on the spin coater over which the solution spreads.

In even other embodiments, the measuring may comprise repeatedly measuring a state of the solution at multiple positions on the spin coater.

Still other embodiments of the present invention provide a method for blood analysis. The method for blood analysis comprises: dropping a solution on a spin coater; applying a certain pressure on a blood cell in the solution; and measuring an elastic modulus of the blood cell by capturing a restoration of the blood cell.

BRIEF DESCRIPTION OF THE DRAWINGS

The accompanying drawings are included to provide a further understanding of the present invention, and are incorporated in and constitute a part of this specification. The drawings illustrate exemplary embodiments of the present invention and, together with the description, serve to explain principles of the present invention. In the drawings:

FIG. 5 is a table showing a hematocrit number according to an embodiment of the present invention.

DETAILED DESCRIPTION OF PREFERRED EMBODIMENTS

Figure 1:
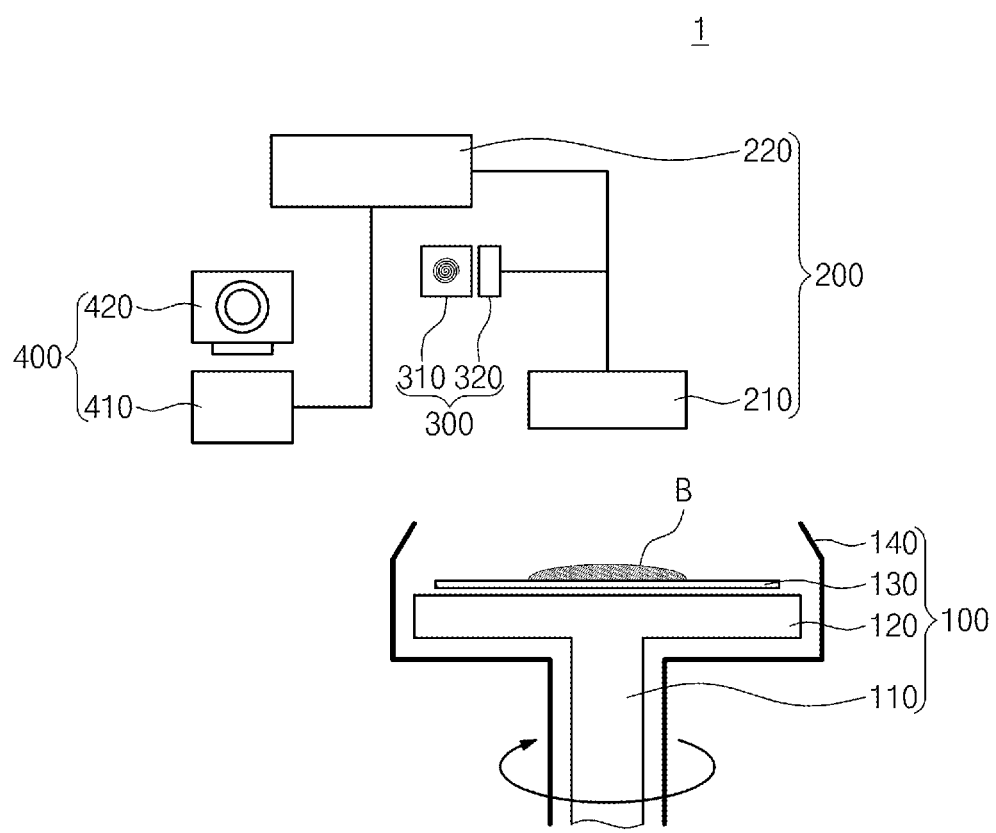
FIG. 1 is a view illustrating an apparatus for blood analysis according to an embodiment of the present invention.

Advantages and features of the present invention, and implementation methods thereof will be clarified through following embodiments described with reference to the accompanying drawings. The present invention may, however, be embodied in different forms and should not be construed as limited to the embodiments set forth herein. Rather, these embodiments are provided so that this disclosure will be thorough and complete, and will fully convey the scope of the present invention to those skilled in the art. Further, the present invention is only defined by scopes of claims. Like reference numerals refer to like elements throughout.

Additionally, the embodiment in the detailed description will be described with sectional views as ideal exemplary views of the present invention. In the figures, the dimensions of layers and regions are exaggerated for clarity of illustration. Accordingly, shapes of the exemplary views may be modified according to manufacturing techniques and/or allowable errors. Therefore, the embodiments of the present invention are not limited to the specific shape illustrated in the exemplary views, but may include other shapes that may be created according to manufacturing processes. For example, an etched region illustrated as a rectangle may have rounded or curved features. Areas exemplified in the drawings have general properties, and are used to illustrate a specific shape of a region of an element. Thus, this should not be construed as limited to the scope of the present invention.

FIG. 1 is a view illustrating an apparatus for blood analysis 1 according to an embodiment of the present invention;

Referring to FIG. 1, the apparatus for blood analysis 1 according to an embodiment of the present invention includes a treatment part 100, a measurement part 200, a light source part 300, and an analysis part 400.

The treatment part 100 may be a spin coater. The spin coater includes a spin shaft 110, a spin chuck 120, a spin substrate 130, and a housing 140. The spin chuck 120 is located on the spin shaft 110. The spin chuck 120 fixedly coupled to the spin shaft 110. The spin substrate 130 is disposed on the spin chuck 120. The spin substrate 130 is fixedly coupled on the spin chuck 120. The spin substrate 130 may be coupled to the spin chuck 120 through a vacuum. Although not shown in FIG. 1, a pressure defined between the spin chuck 120 and the spin substrate 130 may be a vacuum state through a hole in an upper surface of the spin chuck 120. Accordingly, the spin chuck 120 and the spin substrate 130 may be fixedly coupled. A test solution may be dropped on the spin substrate 130. For example, blood B may be dropped on the spin substrate 130. Hereinafter, an operation of the apparatus for blood analysis 1 according to the present invention, when the blood B is dropped on the spin substrate 130, will be described.

The spin substrate 130 may be formed of at least one from among metal, ceramic, polymer, and glass. Here, the polymer may include at least one of polymethyl methacrylate (PMMA), polyimide (PI), polycarbonate (PC) and cyclo olefin copolymer (COC). The polymer may be prepared by a method such as injection molding, hot embossing, extrusion or casting. The spin substrate 130 may have the shape of a circular plate.

Figure 2:
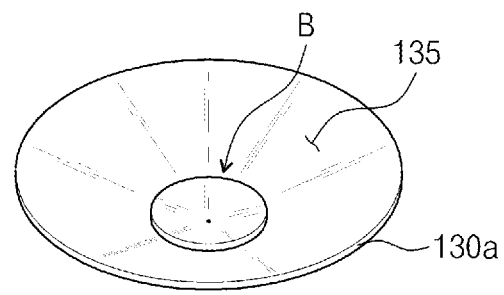
FIG. 2 is a perspective view illustrating a spin coater according to an embodiment of the present invention.

FIG. 2 is a perspective view illustrating a spin coater according to an embodiment of the present invention.

Referring to FIG. 2, the spin substrate 130a may have a concave portion 135 inclined toward a central axis. The spin substrate 130a having a concave portion 135 prevents the blood on the spin substrate 130a from falling to the outside of the spin substrate 130a due to a rotational force of the spin coater 100. The spin chuck 120 may have a recess portion (not shown) into which the concave portion 135 of the spin substrate 130a may be inserted. The spin chuck 120 and the spin substrate 130a may be readily fixedly coupled through a recess portion (not shown).

Figure 3:
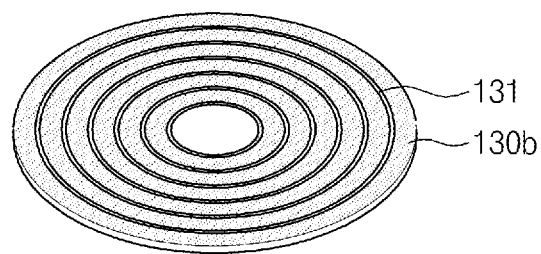
FIG. 3 is a perspective view illustrating a spin coater according to another embodiment of the present invention.

FIG. 3 is a perspective view illustrating a spin coater according to another embodiment of the present invention.

Referring to FIG. 3, in a spin coater of FIG. 3 according to another embodiment of the present invention, the spin substrate 130b may include a ring-shaped groove 131 formed in an upper surface thereof. A plurality of the grooves 131 may be provided on an upper surface of the spin substrate 130b. The plurality of grooves 131 may be provided at regular intervals or may be provided at irregular intervals. The grooves 131 allow the blood B to be spread in a circular plate shape on the spin substrate 130b by increasing a frictional force between the spin substrate 130b and the blood B. The viscosity of the blood B described below may be measured through the area covered by the blood B.

Referring again to FIG. 1, the housing 140 is provided to cover the spin shaft 110, the spin chuck 120, and the spin substrate 130. The housing 140 prevents the blood B from falling out from the spin substrate 130 when the spin substrate rotates.

The light source part 300 emits light onto the blood B on the spin coater 100. The light source part 300 includes a light source 310 and a shutter 320. The light source 310 includes a light emitting diode, an incandescent bulb, or a halogen lamp. The light source 310 emits a white light onto the treatment part 100. The shutter 320 opens/closed the light source 310. A time over which the light is emitted onto blood B is adjusted through the shutter 320. The treatment part 100 may reflect the light, which is emitted from the light source part 300, to the outside.

The measurement part 200 detects an image of the blood B on the spin coater 100. The measurement part 200 includes a light receiving portion 210 and an image processing portion 220. The light receiving portion 210 receives the light reflected from the spin coater 100. The light receiving portion 210 transmits a received light signal to the image processing portion 220. For example, the light receiving portion 210 may be one of a photodiode, a CIS, and a CCD.

Optionally, the light receiving portion 210 may be a camera. The camera captures the varying state of the blood B on the spin coater 100. For example, the camera may capture the degree in which the blood B is spread on the spin coater 100 according to the rotational speed of the spin coater 100, and the color of the blood B on the spin coater 100. Also, pressure may be applied to a blood cell 500 in the blood B by the camera. The image captured by the camera is transmitted to the analysis part 400 described later.

The image processing portion 220 transforms the light, which is received from the light receiving portion 210, into an image signal. The transformed image signal is transmitted to the analysis part 400.

The measurement part 200 may further include a drive portion (not shown) which moves the light receiving part 210 to an upper portion of the spin coater 100. The state of the blood B is measured at multiple positions while the drive portion (not shown) moves the light receiving portion 210. The state of the blood B means the degree of blood B spread on the spin coater 100 according to a rotating speed of the spin coater 100, the color of the blood B according to the volume of the blood cell 500 in the blood B, and the speed in which the blood cell 500 is restored according to the elastic modulus of the blood cell 500 in the blood B. A detailed description will be given later in an embodiment. Blood cells 500 in plasma may not be uniformly distributed. Accordingly, the measured values may be analyzed through averaging or compensation. By means of the analyzed measurements, errors in the measurements according to spatial non-uniformity of the blood cells may be reduced.

The measurement part 200 may further include a light filter (not shown). Before the light emitted onto the blood B is reflected and arrives at the measurement part 200, only light with a wavelength of a predetermined bandwidth may be transmitted by the light filter (not shown). The light filter (not shown) filters the light emitted from the light source 310 and emits light with a desired wavelength onto the blood. Since filtration may be performed for each wavelength, light with various wavelengths may be emitted.

The analysis part 400 analyzes information on blood B, from a detected signal detected by the measurement part 200. The information on blood B means the viscosity of the blood B, the color of the blood B, and the elastic modulus of blood cells in the blood B. The analysis part 400 may include a computer 410 and an image portion 420. The computer 410 analyzes the image signal, and the analyzed signal is confirmed through the image portion 420.

Figure 4A:
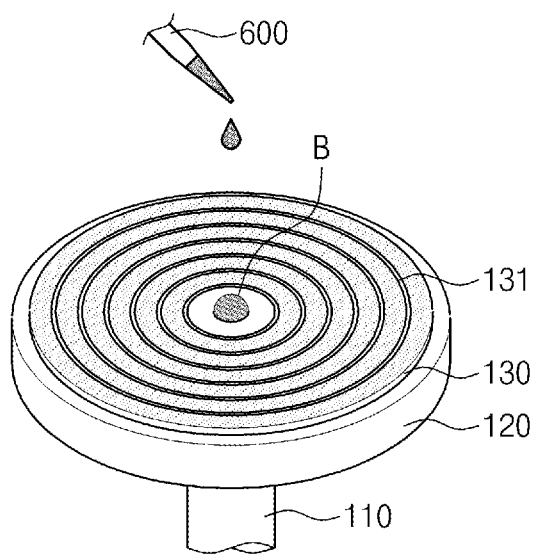
FIGS. 4A through 4C are views illustrating a process of measuring the viscosity of blood in an apparatus for blood analysis according to an embodiment of the present invention.
Figure 4B:
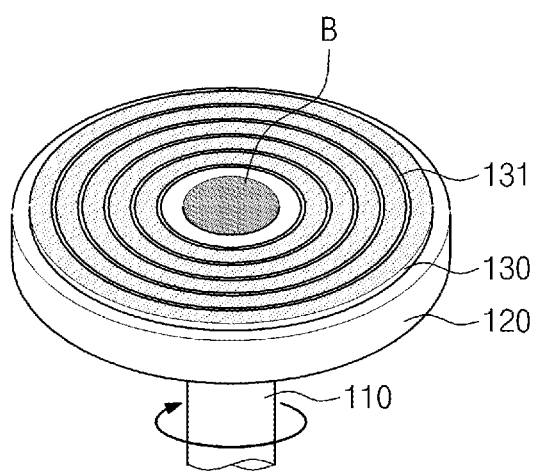
Figure 4C:
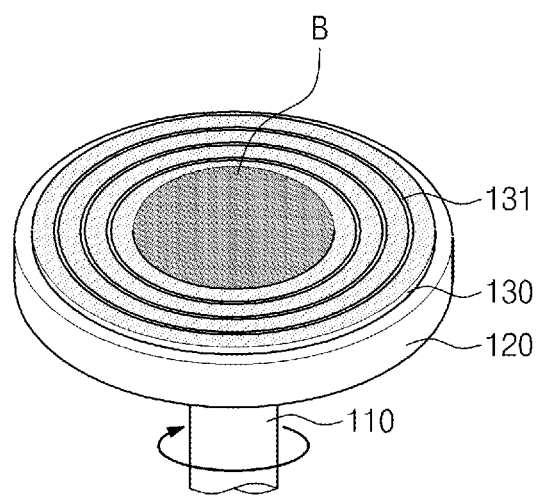

FIGS. 4A through 4C are views illustrating a process of measuring the viscosity of blood in an apparatus for blood analysis according to an embodiment of the present invention.

Referring to FIGS. 4A through 4C, blood B is dropped on the spin coater 100, and then the spin coater 100 is rotated. The viscosity of the blood B is measured while the spin coater 100 is rotated at a gradually increasing speed. The primary components, which determine the viscosity of the blood B, are the blood cells and plasma. The rotational speed of the spin coater 100, the viscosity of the blood B, and the thickness of the blood B are correlated with each other. The greater the rotational speed, the wider the blood is spread on the spin coater 100. In a state of a great rotational speed, the plasma and the blood cells are uniformly coated. The thickness of the blood B is virtually uniform under a constant rotational speed. The coated area differs according to the viscosity of the blood B. Qualitatively, the thickness of the blood B is expressed by an equation as follows.

$$T = \frac{KC^\beta \eta^\gamma}{\omega^\alpha}$$

Here, K is a total compensation constant, C is a suspension concentration, η is an initial liquid viscosity, and ω is a rotational speed. α, β and γ are integers. The thickness of the blood B after rotation at a constant speed for a predetermined time becomes virtually uniform, and the concentration of the blood B is also virtually uniform. As a result, the initial viscosity of the blood B may be measured by measuring a coated area of the blood B.

In FIG. 4A, blood B is dropped on the spin coater 100. The blood B may be supplied by using a spoid 600. The blood B may be optionally supplied by using an injector. When the spin coater 100 is rotated, the blood B is spread as illustrated in FIG. 4B, and when the speed of the spin coater 100 is increased, the blood B is more widely spread as shown in FIG. 4C. The speed of the spin coater 100 is gradually increased. After the speed of the spin coater 100 is increased, the spread area of the blood B is measured while a constant speed is maintained. That is, the spread area of the blood B is measured when ω is constant. When measurements are repeated, errors between each measurement are reduced by allowing the supplied amount of the blood B to be maintained the same.

FIG. 5 is a table showing a hematocrit number according to an embodiment of the present invention Referring to FIG. 5, a hematocrit number may be determined according to the color of blood B. Blood B is dropped on the spin coater 100 and is rotated. The light source part 300 emits light onto the blood B on the spin coater 100. The emitted light is reflected toward a light receiving portion 210 of a measurement part 200. The reflected or transmitted color for the spread portion of the blood B varies according to the volume of red blood cells contained in plasma. When the volume of blood cells in plasma is relatively small, the reflected light approaches an orange color which is the color of plasma. When the volume of blood cells in plasma is relatively large, the reflected light approaches a dark red. The color of the blood B according to the volume of blood cells linearly varies. Accordingly, the hematocrit may be measured by measuring the color of the blood B coated on the spin coater 100.

Figure 6A:
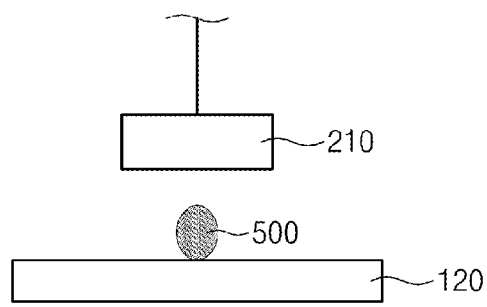
FIGS. 6A through 6C are views illustrating a process of measuring the deformation of blood cells in an apparatus for blood analysis according to the present invention.
Figure 6B:
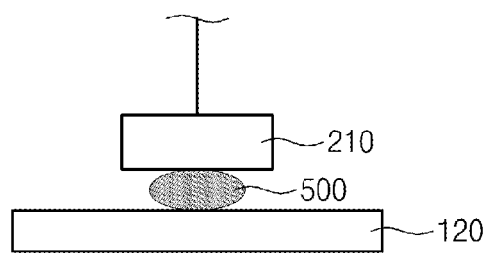
Figure 6C:
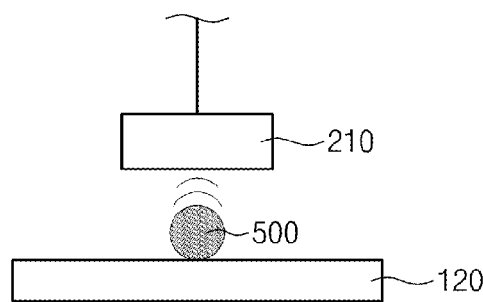

FIGS. 6A through 6C are views illustrating a process of measuring the deformation of blood cells in an apparatus for blood analysis according to the present invention.

Referring to FIGS. 6A through 6C, a blood cell 500 is located on a spin substrate 130. Pressure is applied to the blood cell 500 by using a light receiving portion 210. For example, the light receiving portion 210 may be a camera. A constant pressure is applied to the blood cell 500 for a predetermined time by a lens of the camera. After the predetermined time elapses, the camera lens is lifted. The pressed blood cell 500 is restored to its original shape according to the elastic modulus of the cell. The restoration process is captured by the camera. The speed at which the blood cell 500 is restored is measured through a captured image, and the deformation rate of the blood cell 500 may be measured by analyzing the speed. While the blood cell 500 is restored to its original state, the speed at which the blood cell 500 is restored may be calculated by using the captured image.

Thus, the apparatus for blood analysis 1 according to an embodiment the present invention allows the viscosities of various other fluids to be measured as well as the viscosity of blood.

According to an embodiment of the present invention, an apparatus and a method for blood analysis may be provided which are able to simultaneously measure the viscosity and the hematocrit of blood and the elastic modulus of blood cells.

According to an embodiment of the present invention, an apparatus and a method for blood analysis may be provided which use a spin coater and an optical device so as to have a simple structure and provide a short analysis time.

The above-disclosed subject matter is to be considered illustrative, and not restrictive, and the appended claims are intended to cover all such modifications, enhancements, and other embodiments, which fall within the true spirit and scope of the present invention. Thus, to the maximum extent allowed by law, the scope of the present invention is to be determined by the broadest permissible interpretation of the following claims and their equivalents, and shall not be restricted or limited by the foregoing detailed description.

What is claimed is:

1. An apparatus for blood analysis comprising:
   a spin coater to which a blood is supplied;
   a light source part emitting light to the spin coater;
   a measurement part detecting light reflected from the blood on the spin coater, and outputting a detected signal based on the detected light; and
   an analysis part determining a viscosity of the blood based on the detected signal output from the measurement part.

2. The apparatus of claim 1, wherein the spin coater comprises a spin substrate having a concave portion inclined toward a central axis of the spin substrate.

3. The apparatus of claim 2, wherein the spin substrate includes at least one of metal, ceramic, polymer, and glass.

4. The apparatus of claim 3, wherein the polymer includes at least one of polymethyl methacrylate (PMMA), polyimide (PI), polycarbonate (PC) and cyclo olefin copolymer (COC).

5. The apparatus of claim 1, wherein the spin coater comprises a spin substrate having at least one or more ring-shaped grooves spaced apart from each other.

6. The apparatus of claim 5, wherein the measurement part obtains images of the blood spread on the substrate and the grooves of the rotating spin coater, and
   wherein the analysis part determines the viscosity of the blood based on the images.

7. The apparatus of claim 1, wherein the analysis part determines a color of the blood from the detected signal, and determines a volume of blood cells in the blood corresponding to the color.

8. The apparatus of claim 1, wherein the measurement part continuously captures deformation of a blood cell in the blood by momentarily supplying a pressure to the blood cell.

9. The apparatus of claim 1, wherein the measurement part comprises:
   a light receiving portion receiving light reflected from the spin coater; and
   an image processing portion transforming the light received by the light receiving portion into an image signal.

10. The apparatus of claim 9, wherein the light receiving portion comprises one of a photodiode, a CIS, and a CCD.

11. The apparatus of claim 10, wherein the measurement part further comprises a drive portion which moves the light receiving portion toward the spin coater.

12. The apparatus of claim 1, wherein the analysis part determines a color of the blood and an elastic modulus of blood cells in the blood.

13. A method for blood analysis, the method comprising:
    dropping blood on a spin coater;
    rotating the spin coater;
    measuring a varying state of the blood when the spin coater rotates; and
    determining a viscosity of the blood based on the varying state.

14. The method of claim 13, wherein the varying state includes an area of the blood spread on the spin coater.

15. The method of claim 13, wherein the rotating of the spin coater comprises gradually increasing a rotational speed of the spin coater.

16. The method of claim 13, further comprising:
    measuring a reflected color of the blood spread on the spin coater after emitting light onto a portion on the spin coater; and
    determining a hematocrit of the blood based on the reflected color.

17. The method of claim 13, wherein measuring the varying state comprises repeatedly measuring the varying state of the blood at multiple positions on the spin coater.

18. A method for blood analysis, the method comprising:
    dropping blood on a spin coater;
    applying a predetermined pressure to a blood cell in the blood;
    measuring a rate of deformation of the blood cell by capturing a restoration of the blood cell;
    rotating the spin coater;
    measuring an area of the blood on the spin coater; and
    determining a viscosity of the blood based on the measured area.

* * * * *